United States Patent
Brainard et al.

(10) Patent No.: US 8,350,078 B2
(45) Date of Patent: Jan. 8, 2013

(54) METHODS FOR MAKING STERICALLY HINDERED ETHERS

(75) Inventors: Robert L. Brainard, Albany, NY (US); Brian Cardineau, West Islip, NY (US)

(73) Assignee: The Research Foundation of State University of New York, Albany, NY (US)

( * ) Notice: Subject to any disclaimer, the term of this patent is extended or adjusted under 35 U.S.C. 154(b) by 228 days.

(21) Appl. No.: 12/869,220

(22) Filed: Aug. 26, 2010

(65) Prior Publication Data

US 2011/0152570 A1    Jun. 23, 2011

Related U.S. Application Data

(60) Provisional application No. 61/237,132, filed on Aug. 26, 2009.

(51) Int. Cl.
*C07C 67/14* (2006.01)
*C07C 43/10* (2006.01)

(52) U.S. Cl. ........ 560/263; 560/264; 568/613; 568/619; 568/623

(58) Field of Classification Search .................. None
See application file for complete search history.

(56) References Cited

FOREIGN PATENT DOCUMENTS

WO      2009105667       8/2009

OTHER PUBLICATIONS

Ogawa et al, Studies in Surface Science, Adsorption of Diols on Silica Gel Surface and Their Reactivities for Selective Monoacetylation with Acetyl Chloride, 2001, 132, pp. 1075-1078.*
Notheisz et al, Acta Physica et Chemica, Chemical Transformations of Diols and Cyclic Ether. XXXIII. Reactions of Diols with Acid Chlorides, 1972, 18(1-2), pp. 89-98.*
U.S. Appl. No. 12/918,647, filed Aug. 20, 2010 (Not yet published).
U.S. Appl. No. 12/869,308, filed Aug. 26, 2010 (Not yet published).
U.S. Appl. No. 12/869,202, filed Aug. 26, 2010 (Not yet published).

* cited by examiner

*Primary Examiner* — Paul A Zucker
(74) *Attorney, Agent, or Firm* — Heslin Rothenberg Farley & Mesiti P.C.

(57) ABSTRACT

The present invention relates to processes for the production of sterically hindered diol ethers and diacyl ethers of formula

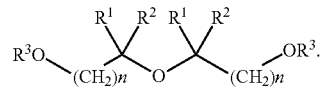

20 Claims, No Drawings

METHODS FOR MAKING STERICALLY HINDERED ETHERS

CROSS REFERENCE TO RELATED APPLICATION

This application claims benefit of priority from U.S. Provisional Patent Application No. 61/237,132, filed Aug. 26, 2009, the entire contents of which are incorporated herein by reference.

FIELD OF THE INVENTION

The present invention relates to processes for the production of sterically hindered ethers and to the ethers so produced.

BACKGROUND OF THE INVENTION

Photolithography or optical lithography is a process used, inter alia, in semiconductor device fabrication to transfer a pattern from a photomask (sometimes called reticle) to the surface of a substrate. At present, it is desired to use light in the extreme UV range (13.5 nm or shorter) for photolithography of circuits having line widths of 32-20 nm, for which it has been proposed to utilize "chemically amplified" photoresists. The idea is to include in the photoresist an amount of a thermally stable, photolytically activated acid precursor (sometimes called a "photoacid generator" or "PAG"), so that upon irradiation, acid will be generated. The polymer in the photoresist is chosen to be acid labile so that the acid from the PAG will cleave the polymer. In a variation, it has been proposed to include in the resist composition—in addition to the photoacid generator—an acid precursor (sometimes referred to as an "acid amplifier") which is (a) photolytically stable and (b) thermally stable in the absence of acid but thermally active in the presence of acid. In such systems, during radiation exposure the PAG generates acid, which then during post-exposure bake acts as a catalyst to activate the acid-amplifier. Such systems are sometimes referred to in the literature as "acid amplifier" systems, since the catalytic action of the photolytically-generated acid on the second acid precursor during post-exposure bake results in an effective number of acid molecules which is higher than the number of photons absorbed during radiation exposure, thus effectively "amplifying" the effect of exposure and amplifying the amount of acid present.

Among the difficulties encountered in trying to implement chemical amplification photoresists systems is "outgassing", a process whereby, as a result of acid formation, gas is generated, leading to volatile compounds that can leave the resist film while the wafer is still in the exposure tool. Outgassing can occur under ambient conditions or under vacuum as is used with extreme ultraviolet (EUV) lithography. Outgassing is a problem because the small molecules can deposit on the optics (lenses or mirrors) of the exposure tool and cause a diminution of performance. Furthermore, there is a trade-off between resolution, line-width roughness and sensitivity. A resist's resolution is typically characterized as the smallest feature the resist can print. Line width roughness is the statistical variation in the width of a line. Sensitivity is the dose of radiation required to print a specific feature on the resist, and is usually expressed in units of $mJ/cm^2$.

PCT application PCT/US09/34707 filed Feb. 20, 2009 discloses a new resist system based on a polymer with PAG and ester functionality located within the main polymer chain. When the PAG breaks apart photochemically or the ester-linkages break apart by acidolysis, the molecular weight of the polymer decreases, allowing for higher acid diffusion during bake and faster resist dissolution during development. Acid-labile diols are useful monomers for incorporating in such polymers.

SUMMARY OF THE INVENTION

The invention disclosed herein relates to a new group of compounds that can be synthesized in high yields, with high purity, from inexpensive starting materials. The compounds are exquisitely sensitive to acid and fragment very easily. These compounds can be used to produce high resolution starting materials for use in several different areas of photolithography.

The diol compounds of the invention can be made with inexpensive starting materials and can then be combined with:

a. Diacyl chlorides to make acid cleavable polymers (2);

b. Diacyl chlorides and PAG diols to make chain scission polyester PAG-polymers ($CSP^3$) (3);

c. Sulfonyl chlorides to make diacid amplifiers (4); and d. Disulfonyl chlorides to make polyacid amplifiers (5).

One exemplary diol is shown below:

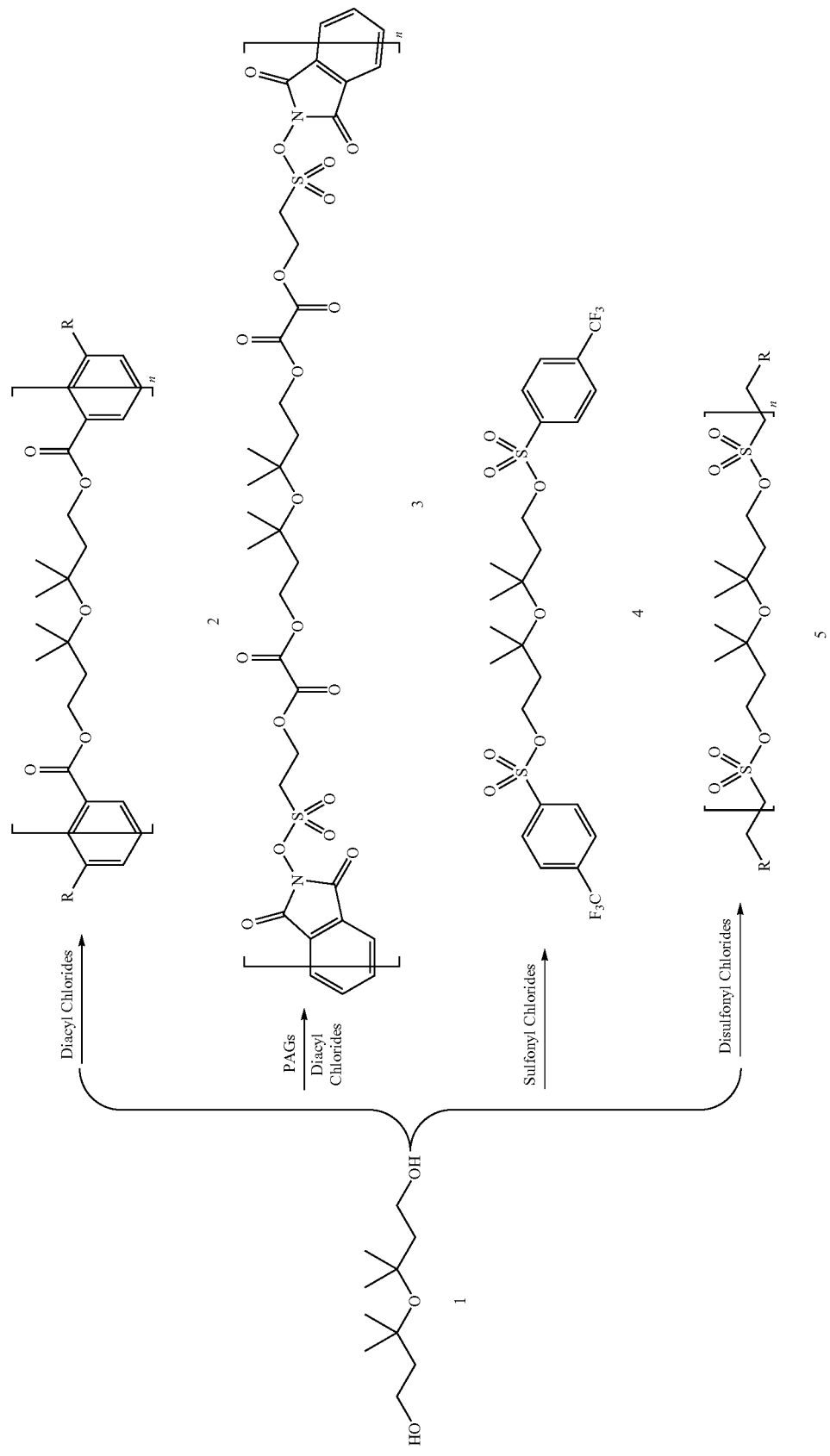

In one embodiment, the invention relates to a process for preparing a compound of formula

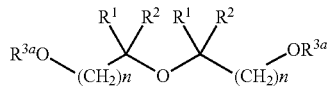

wherein
$R^1$ and $R^2$ are independently chosen from $C_1$-$C_6$ alkyl, or $R^1$ and $R^2$ together with the carbon to which they are attached form a cyclopentane or cyclohexane ring;
$R^{1a}$ is —C(O)$R^4$;
$R^4$ is chosen from $C_1$-$C_3$ alkyl, phenyl, and phenyl substituted with methyl or halogen; and
n is 1 to 4;
said process comprising reacting a diol of formula

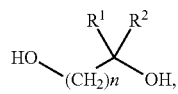

optionally in the presence of a catalyst, with an acid halide of formula $R^4COX^a$ wherein $X^a$ is fluoro, chloro or bromo.

In one embodiment, the invention relates to a process for preparing a diol ether of formula

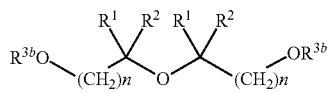

wherein
$R^1$ and $R^2$ are independently chosen from $C_1$-$C_6$ alkyl, or $R^1$ and $R^2$ together with the carbon to which they are attached form a cyclopentane or cyclohexane ring;
$R^{3b}$ is H; and
n is 1 to 4;
said process comprising
(1) reacting a diol of formula

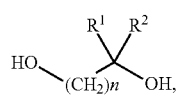

optionally in the presence of a catalyst, with an acid halide of formula $R^4COX^a$ wherein $R^4$ is chosen from $C_1$-$C_3$ alkyl, phenyl, and phenyl substituted with methyl or halogen and $X^a$ is fluoro, chloro or bromo to provide a diacyl ether of formula:

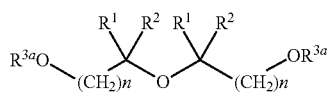

wherein
$R^{1a}$ is —C(O)$R^4$, and;
(2) reacting said diacyl ether with aqueous base in a polar organic solvent to provide said diol ether.

In another embodiment, the invention relates to compounds of formula

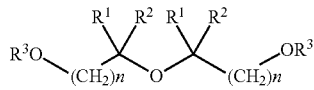

wherein
$R^1$ and $R^2$ are independently chosen from $C_1$-$C_6$ alkyl, or $R^1$ and $R^2$ together with the carbon to which they are attached form a cyclopentane or cyclohexane ring;
$R^3$ is chosen from hydrogen and —C(O)$R^4$;
$R^4$ is chosen from $C_1$-$C_3$ alkyl, phenyl, and phenyl substituted with methyl or halogen; and
n is 1 to 4.

DETAILED DESCRIPTION OF THE INVENTION

In one embodiment, the invention relates to a process for preparing a compound of formula

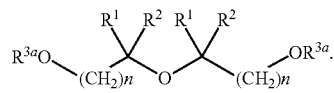

This process comprises reacting a diol of formula

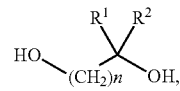

with an acid halide of formula $R^4COX^a$. In some embodiments, $X^a$ is fluoro. In other embodiments, $X^a$ is chloro. In still other embodiments, $X^a$ is bromo. Because of the ready availability of acyl chlorides, $X^a$ is most commonly Cl.

$R^{3a}$ is —C(O)$R^4$. In some embodiments, $R^4$ is $C_1$-$C_3$ alkyl. In other embodiments, $R^4$ is phenyl. In further embodiments, $R^4$ is phenyl substituted with methyl or halogen.

In some embodiments, n is 1. In other embodiments, n is 2. In still other embodiments, n is 3. In certain embodiments, n is 4.

In some embodiments, the process takes place in the presence of a catalyst. It has been found that, although the reaction works in the absence of catalyst, the yields are often improved with the addition of a catalyst.

In some embodiments, $R^1$ and $R^2$ are independently chosen from $C_1$-$C_6$ alkyl. In some of these embodiments, $R^1$ and $R^2$ are chosen from methyl and ethyl. In other embodiments, $R^1$ and $R^2$ together with the carbon to which they are attached form a cyclopentane or cyclohexane ring.

In another embodiment, the invention relates to a process for preparing a diol ether of formula

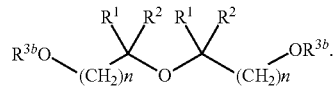

This process comprises reacting a diol of formula

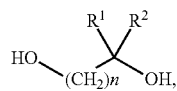

with an acid halide of formula $R^4COX^a$ to provide a diacyl ether of formula

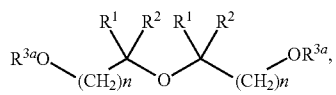

which is then reacted in aqueous base in a polar organic solvent to provide the diol ether.

Polar organic solvents include alkanols (e.g. methanol, ethanol, n-propanol, isopropanol), dioxane, methoxyethanol, dimethoxyethane, THF, DMF, acetonitrile and DMSO. In certain embodiments, the polar organic solvent is methanol and the base is ammonia.

In some embodiments, $X^a$ is fluoro. In other embodiments, $X^a$ is chloro. In still other embodiments, $X^a$ is bromo.

$R^{3b}$ is H. $R^{3a}$ is —C(O)R$^4$. In some embodiments, $R^4$ is $C_1$-$C_3$ alkyl. In other embodiments, $R^4$ is phenyl. In further embodiments, $R^4$ is phenyl substituted with methyl or halogen.

In some embodiments, n is 1. In other embodiments, n is 2. In still other embodiments, n is 3. In certain embodiments, n is 4.

In some embodiments, the process takes place in the presence of a catalyst.

In some embodiments, $R^1$ and $R^2$ are independently chosen from $C_1$-$C_6$ alkyl. In some of these embodiments, $R^1$ and $R^2$ are chosen from methyl and ethyl. In other embodiments, $R^1$ and $R^2$ together with the carbon to which they are attached form a cyclopentane or cyclohexane ring.

In some embodiments of the processes described above a catalyst is present and the catalyst is $ZrX^b{}_2O$. In other embodiments, the catalyst is $ZrX^b{}_4$. In still other embodiments, the catalyst is $HfX^b{}_2O$ or $HfX^b{}_4$. In certain embodiments, the catalyst is $TiX^b{}_2O$ or $TiX^b{}_4$. In yet other embodiments, the catalyst is $MgBr_2$. In other embodiments, the catalyst is $ZnCl_2$ or $ZnBr_2$. In yet other embodiments, the catalyst is $Sc(OTf)_3$.

In some of the above embodiments, $R^4$ is $CH_3$ and $X^a$ is chloro.

In another aspect, the invention relates to compounds of formula

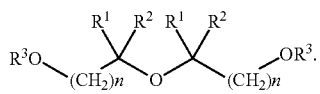

In some of these embodiments, $R^1$ and $R^2$ are independently chosen from $C_1$-$C_6$ alkyl. In certain embodiments, $R^1$ and $R^2$ are both methyl. In other embodiments, $R^1$ and $R^2$ together with the carbon to which they are attached, form a cyclopentane or cyclohexane ring.

In other embodiments, $R^3$ is hydrogen and the compound is of formula

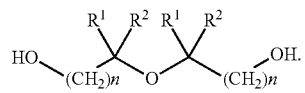

In some embodiments, $R^3$ is —C(O)R$^4$ and the compound is of formula

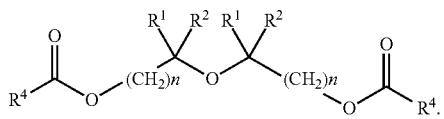

In some embodiments, $R^4$ is $C_1$-$C_3$ alkyl. In certain embodiments, $R^4$ is methyl. In other embodiments, $R^4$ is phenyl. In further embodiments, $R^4$ is phenyl substituted with methyl or halogen.

In some embodiments, n is 1. In other embodiments, n is 2. In still other embodiments, n is 3. In yet other embodiments, n is 4.

In some embodiments, $R^3$ is —C(O)R$^4$ and n is 2. In still other embodiments, $R^4$ is methyl.

In certain embodiments, $R^3$ is hydrogen and n is 2.

In still other embodiments, $R^1$ and $R^2$ are both methyl.

DEFINITIONS

Throughout this specification the terms and substituents retain their definitions.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below.

Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ Hydrocarbon includes alkyl, cycloalkyl, polycycloalkyl, alkenyl, alkynyl, aryl and combinations thereof. Examples include benzyl, phenethyl, cyclohexylmethyl, camphoryl and naphthylethyl. The term "carbocycle" is intended to include ring systems consisting entirely of carbon but of any oxidation state. Thus ($C_3$-$C_{10}$) carbocycle refers to such systems as cyclopropane, benzene and cyclohexene; ($C_8$-$C_{12}$) carbopolycycle refers to such systems as norbornane, decalin, indane and naphthalene.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. Methoxy is preferred. For the purpose of this application, alkoxy and lower alkoxy include methylenedioxy and ethylenedioxy.

The term "halogen" means fluorine, chlorine, bromine or iodine.

Terminology related to "protecting", "deprotecting" and "protected" functionalities may occur in this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups".

In the case of the present invention, the functionalities that are protected include alcohols. Suitable groups are discussed in standard textbooks in the field of chemistry, such as *Protective Groups in Organic Synthesis* by T. W. Greene and P. G. M. Wuts [John Wiley & Sons, New York, 1999], which is incorporated herein by reference.

Synthesis 3,3'-oxybis(3-methylbutan-1-yl)diacetate

To an oven-dried flask containing a catalytic amount of zirconium(IV) oxychloride octahydrate, under nitrogen was added 3-methylbutane-1,3-diol (2.500 g, 24 mmol) and methylene chloride (50 mL). While stirring, acetyl chloride (5.652 g, 72 mmol) was added dropwise over 20 minutes using a syringe pump. Let stir overnight, then worked up by washing with 5% sodium carbonate (2×50 mL) then brine (1×50 mL), dried over sodium sulfate, filtered and dried under reduced pressure. The product was a viscous clear yellow oil (1.763 g yield). $^1$H NMR (400 MHz, CDCl$_3$): δ 1.59 (s, 12H), 2.02 (s, 6H), 2.08 (t, J=6.9, 4H), 4.28 (t, J=6.9, 4H).

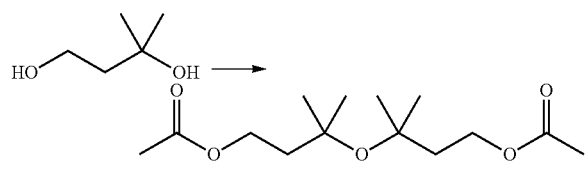

3,3'-oxybis(3-methylbutan-1-ol)

To a flask containing 3,3'-oxybis(3-methylbutan-1-yl)diacetate (0.274 g, 1 mmol), was added 10 mL of 2.0N methanolic ammonia and the reaction was stirred overnight at room temperature. Solvent was then removed under reduced pressure. Compound was then dissolved in 20 mL diethyl ether and precipitate was filtered out. Filtrate was then reduced under vacuum to yield a colorless liquid. (0.187 g yield) $^1$H NMR (400 MHz, CDCl$_3$): δ 1.61 (s, 12H), 2.04 (t, J=6.6, 4H), 3.88 (t, J=6.6, 4H).

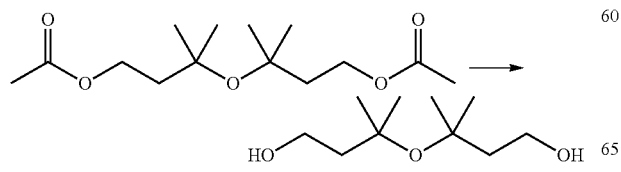

Although this invention is susceptible to embodiment in many different forms, preferred embodiments of the invention have been shown. It should be understood, however, that the present disclosure is to be considered as an exemplification of the principles of this invention and is not intended to limit the invention to the embodiments illustrated.

We claim:

1. A process for preparing compound of formula

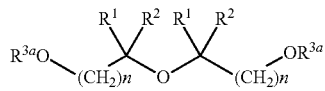

wherein

R$^1$ and R$^2$ are independently chosen from C$_1$-C$_6$ alkyl, or R$^1$ and R$^2$ together with the carbon to which they are attached form a cyclopentane or cyclohexane ring;

R$^{3a}$ is —C(O)R$^4$;

R$^4$ is chosen from C$_1$-C$_3$ alkyl, phenyl, and phenyl substituted with methyl or halogen; and n is 1 to 4;

said process comprising reacting a diol of formula

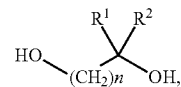

optionally in the presence of a catalyst, with an acid halide of formula R$^4$COX$^a$, wherein X$^a$ is fluoro, chloro or bromo.

2. A process for preparing a diol ether of formula

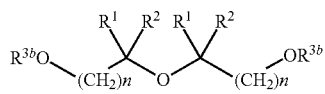

wherein

R$^1$ and R$^2$ are independently chosen from C$_1$-C$_6$ alkyl, or R$^1$ and R$^2$ together with the carbon to which they are attached form a cyclopentane or cyclohexane ring;

R$^{3b}$ is H; and n is 1 to 4;

said process comprising (1) reacting a diol of formula

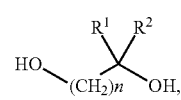

optionally in the presence of a catalyst, with an acid halide of formula R$^4$COX$^a$ wherein R$^4$ is chosen from C$_1$-C$_3$ alkyl, phenyl, and phenyl substituted with methyl or halogen and X$^a$ is fluoro, chloro or bromo to provide a diacyl ether of formula:

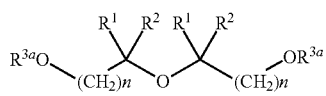

wherein
$R^{3a}$ is —C(O)$R^4$, and;
(2) reacting said diacyl ether with aqueous base in a polar organic solvent to provide said diol ether.

3. A process according to claim 2 wherein said polar organic solvent is methanol and said base is ammonia.

4. A process according to claim 1, wherein said catalyst, when present, is chosen from $ZrX^b_2O$, $ZrX^b_4$, $HfX^b_2O$, $HfX^b_4$, $TiX^b_2O$, $TiX^b_4$, $MgBr_2$, $ZnCl_2$, $ZnBr_2$ and $Sc(OTf)_3$, wherein $X^b$ is selected from fluoro, chloro, bromo and iodo.

5. A process according to claim 1, wherein $R^4$ is $CH_3$ and $X^a$ is chloro.

6. A process according to claim 4 wherein said catalyst is $ZrCl_2O$.

7. A process according to claim 1 wherein $R^1$ and $R^2$ are chosen from methyl and ethyl.

8. A process according to claim 1 wherein n is 2.

9. A compound of formula

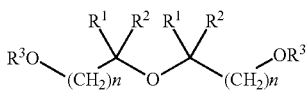

wherein
$R^1$ and $R^2$ are independently chosen from $C_1$-$C_6$ alkyl, or $R^1$ and $R^2$ together with the carbon to which they are attached form a cyclopentane or cyclohexane ring;
$R^3$ is chosen from hydrogen and —C(O)$R^4$;
$R^4$ is chosen from $C_1$-$C_3$ alkyl, phenyl, and phenyl substituted with methyl or halogen; and
n is 1 to 4.

10. A compound according to claim 9 of formula

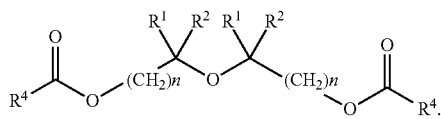

11. A compound according to claim 10 of formula

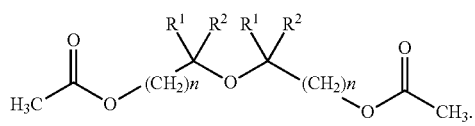

12. A compound according to claim 11 of formula

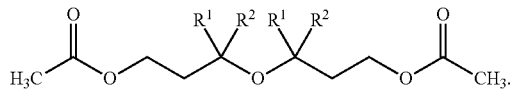

13. A compound according to claim 9 of formula

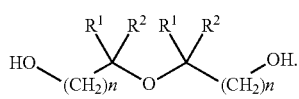

14. A compound according to claim 13 of formula

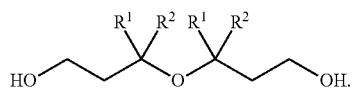

15. A compound according to claim 9 wherein $R^1$ and $R^2$ are $CH_3$.

16. A process according to claim 2 wherein said catalyst, when present, is chosen from $ZrX^b_2O$, $ZrX^b_4$, $HfX^b_2O$, $HfX^b_4$, $TiX^b_4$, $MgBr_2$, $ZnCl_2$, $ZnBr_2$ and $Sc(OTf)_3$, wherein $X^b$ is selected from fluoro, chloro, bromo and iodo.

17. A process according to claim 16 wherein said catalyst is $ZrCl_2O$.

18. A process according to claim 3 wherein said catalyst, when present, is chosen from $ZrX^b_2O$, $ZrX^b_4$, $HfX^b_2O$, $HfX^b_4$, $TiX^b_2O$, $TiX^b_4$, $MgBr_2$, $ZnCl_2$, $ZnBr_2$ and $Sc(OTf)_3$, wherein $X^b$ is selected from fluoro, chloro, bromo and iodo.

19. A process according to claim 2 wherein $R^4$ is $CH_3$ and $X^a$ is chloro.

20. A process according to claim 3 wherein $R^4$ is $CH_3$ and $X^a$ is chloro.

* * * * *

UNITED STATES PATENT AND TRADEMARK OFFICE
CERTIFICATE OF CORRECTION

PATENT NO. : 8,350,078 B2
APPLICATION NO. : 12/869220
DATED : January 8, 2013
INVENTOR(S) : Brainard et al.

Page 1 of 1

It is certified that error appears in the above-identified patent and that said Letters Patent is hereby corrected as shown below:

Column 12, Line 37: Claim 16, Delete "$HfX^b_4$, $TiX^b_4$, $MgBr_2$" and insert --$HfX^b_4$, $TiX^b_2O$, $TiX^b_4$, $MgBr_2$--

Signed and Sealed this
Twelfth Day of March, 2013

Teresa Stanek Rea
*Acting Director of the United States Patent and Trademark Office*